(12) United States Patent
Schmidt et al.

(10) Patent No.: US 11,154,666 B2
(45) Date of Patent: Oct. 26, 2021

(54) VAPORISER HEAD FOR AN INHALER, IN PARTICULAR FOR AN ELECTRONIC CIGARETTE PRODUCT

(71) Applicant: HAUNI MASCHINENBAU GMBH, Hamburg (DE)

(72) Inventors: Rene Schmidt, Buchholz i.d.N. (DE); Gunnar Niebuhr, Hamburg (DE); Lasse Cornils, Hamburg (DE)

(73) Assignee: HAUNI MASCHINENBAU GMBH, Hamburg (DE)

( * ) Notice: Subject to any disclaimer, the term of this patent is extended or adjusted under 35 U.S.C. 154(b) by 296 days.

(21) Appl. No.: 16/458,101

(22) Filed: Jun. 30, 2019

(65) Prior Publication Data
US 2020/0008473 A1 Jan. 9, 2020

(30) Foreign Application Priority Data

Jul. 9, 2018 (DE) .......................... 102018116549.8
Nov. 8, 2018 (DE) .......................... 102018127926.4

(51) Int. Cl.
*A24F 47/00* (2020.01)
*A61M 15/00* (2006.01)
*A61M 11/04* (2006.01)
*F17C 9/02* (2006.01)

(52) U.S. Cl.
CPC ...... *A61M 15/0021* (2014.02); *A61M 11/042* (2014.02); *F17C 9/02* (2013.01)

(58) Field of Classification Search
CPC ............. A24F 47/008; A61M 15/0021; A61M 11/0042; F17C 9/02

USPC ........................................................ 131/329
See application file for complete search history.

(56) References Cited

U.S. PATENT DOCUMENTS

| 2,860,638 A * | 11/1958 | Bartolomeo | A24F 42/20 |
| | | | 128/202.21 |
| 9,730,473 B2 * | 8/2017 | Shinkawa | B65D 85/70 |
| 10,874,139 B2 * | 12/2020 | Alvarez | A61M 15/003 |

(Continued)

FOREIGN PATENT DOCUMENTS

| DE | 10 2014 114 133 A1 | 3/2016 |
| DE | 10 2016 120 803 A1 | 3/2016 |

(Continued)

OTHER PUBLICATIONS

European Search Report issued by the European Patent Office dated Dec. 11, 2019 for parallel European Patent Application No. 19 181 228.8.

(Continued)

*Primary Examiner* — Neil Abrams
(74) *Attorney, Agent, or Firm* — Saliwanchik, Lloyd & Eisenschenk (57) ABSTRACT

The invention relates to a vaporiser head for an inhaler, in particular for an electronic cigarette product, comprising a heating element-wick structure assembly consisting of an electrically operable heating element, which has at least one liquid-conducting through-channel and a porous and/or capillary wick structure arranged at an inlet side of the heating element, and a support plate for retaining the heating element-wick structure assembly. The vaporiser head has a liquid-conducting cannula having a preferably protruding piercing region.

27 Claims, 5 Drawing Sheets

(56) References Cited

U.S. PATENT DOCUMENTS

| | | | |
|---|---|---|---|
| 2015/0040929 A1* | 2/2015 | Hon | A24F 40/42 |
| | | | 131/329 |
| 2017/0215478 A1* | 8/2017 | Harrison | A24F 40/48 |
| 2019/0246696 A1 | 8/2019 | Schmidt et al. | |
| 2019/0328039 A1* | 10/2019 | Romming | A24F 40/70 |
| 2020/0008473 A1* | 1/2020 | Schmidt | A61M 15/06 |
| 2020/0046020 A1* | 2/2020 | Cross | A61M 15/0005 |
| 2020/0260788 A1* | 8/2020 | Cornils | H05B 3/44 |
| 2021/0186097 A1* | 6/2021 | Schmidt | A61M 15/06 |
| 2021/0186100 A1* | 6/2021 | Trieu | A24F 40/51 |

FOREIGN PATENT DOCUMENTS

| | | |
|---|---|---|
| WO | WO 2010/045671 A1 | 4/2010 |
| WO | WO 2017/167521 A1 | 10/2017 |
| WO | WO 2019/072915 A1 | 4/2019 |
| WO | WO 2019/072969 A1 | 4/2019 |
| WO | WO 2019/072971 A1 | 4/2019 |

OTHER PUBLICATIONS

Examination Report issued by the German Patent Office dated Aug. 5, 2021 for parallel German Patent Application No. 10 2018 127 926.4 with an English translation.

* cited by examiner

VAPORISER HEAD FOR AN INHALER, IN PARTICULAR FOR AN ELECTRONIC CIGARETTE PRODUCT

CROSS REFERENCE TO A RELATED APPLICATION

This application claims priority under 35 U.S.C. § 119(e) of German Patent Application No. DE 10 2018 116 549.8, filed Jul. 9, 2018 and German Patent Application No. DE 10 2018 127 926.4, filed Nov. 8 2018; both of which are incorporated herein by reference in their entirety.

FIELD OF THE INVENTION

The present invention relates to a vaporiser head for an inhaler, in particular for an electronic cigarette product, comprising a heating element-wick structure assembly having an electrically operable heating element, which has at least one liquid-conducting through-channel and a porous and/or capillary wick structure arranged at an inlet side of the heating element, and a support plate for retaining the heating element-wick structure assembly. The invention also relates to a consumption unit, to a liquid reservoir, to an inhaler and to a method for producing a ready-to-use consumption unit.

BACKGROUND OF THE INVENTION

Inhalers, and in particular electronic cigarette products based on the wick-filament principle, are known in the prior art. Liquid from a liquid reservoir is fed to a vaporiser unit or vaporiser head and is vaporised by the heating element and fed to an air stream as vapour and/or aerosol. Vaporiser units based on the wick-filament principle often lead to inconsistent vaporisation, bubble formation, local overheating, dry running and dirt, for example.

In the prior art, inhalers comprise either an open or a closed liquid reservoir.

In open tank systems, a user can top up liquid. In this case, the user is responsible for checking the type of liquid and the use. When used regularly, the vaporiser head must be swapped since the wick structure in particular becomes dirty due to residues caused by local overheating in the immediate vicinity of the heating element and significantly alters the taste of the aerosol. In addition, inhalers having open tank systems can be improperly used through the use of any given liquids; this may pose health risks for consumers.

These disadvantages are overcome by a closed tank system. In a closed-tank system, a cartridge comprises a liquid reservoir filled with liquid, and a vaporiser head non-detachably connected to the liquid reservoir. The user uses up or fully vaporises the cartridge contents and then disposes of the cartridge, even if the vaporiser head is in a state not yet affected by residues and/or is still functional. The non-detachable connection of the vaporiser head to the liquid reservoir only allows the entire cartridge to be disposed of.

BRIEF SUMMARY OF THE INVENTION

The problem addressed by the invention is that of providing a vaporiser head having improved connection options.

To solve the problem, the invention proposes a vaporiser head according to independent claim 1.

According to the invention, the vaporiser head has a liquid-conducting cannula that has a preferably protruding piercing region. The liquid-conducting cannula is an easy-to-handle option for establishing a hydraulic connection between the vaporiser head and an external component, in particular a liquid tank or liquid reservoir. By means of the liquid-conducting cannula, the liquid reservoir can be tapped and liquid supplied to the vaporiser head. By means of the cannula, liquid from the liquid reservoir can be delivered from the piercing region to the heating element-wick structure assembly in order to be able to deliver the liquid from the liquid reservoir to the wick structure and/or to the heating element. Advantageously, the piercing region protrudes beyond the vaporiser head in order for the cannula to be able to pierce an external component, for example a liquid tank.

On the basis of the invention, the consumer can produce a ready-to-use unit comprising a vaporiser head and liquid reservoir in a simple manner, and swap the vaporiser head in a simple manner. Therefore, the vaporiser head can also be referred to as a removable vaporiser.

In particular, the cannula according to the invention is tubular; however, it is not limited to a specific, e.g. round, cross-sectional shape, but rather covers all conceivable and suitable cross-sectional shapes.

Advantageously, the cannula comprises a tube that is open on both sides and through which liquid can be transported. At one open side, or the pricking side, the cannula has the piercing region, and at the other open side, or attachment side, opposite the piercing region, the cannula is attached to the support plate and/or to the heating element-wick structure assembly. Between the two sides, i.e. the pricking side and the attachment side, a liquid-conducting channel advantageously extends within the cannula, in which channel liquid can be delivered from the piercing region or pricking side to the wick structure, heating element and/or attachment side.

At the attachment side, the cannula is attached to the support plate and/or to the heating element-wick structure assembly. The attachment between the cannula and the support plate or heating element-wick structure assembly can, for example, involve clamping of the cannula in a through-opening in the support plate, clamping of the cannula by clamping members arranged on the support plate or heating element-wick structure assembly, adhesive bonding and/or welding. In one embodiment, the support plate and the cannula are formed in a single piece, i.e. they consist of the same material and together form a single component. Preferably, the cannula is attached to the support plate and/or to the heating element-wick structure assembly such that it cannot be detached by the user.

Advantageously, the cannula forms an angle of, for example, 30° to 90°, preferably 45° to 90°, and more preferably of 90°, with the preferably at least locally planar support plate so as to ensure advantageous alignment of the cannula.

In a preferred embodiment, the wick structure and/or the heating element is/are arranged on an attachment side of the cannula to ensure that liquid is delivered reliably, the wick structure and/or the heating element can be arranged in a manner retainable by the support plate, and/or vaporised liquid can be advantageously fed at the outlet side as aerosol or vapour. Advantageously, the wick structure can extend into the cannula, for example by at least 25%, preferably at least 50%, even more preferably at least 75%, based on the length of the cannula. In other embodiments, however, the wick structure can also extend through the entire cannula. In this embodiment, the heating element-wick structure assembly is arranged on an end of the cannula or tube whilst the other free end remains open in order to receive liquid from the liquid reservoir.

Advantageously, the wick structure is arranged at least in part within the cannula so as to ensure effective construction of the vaporiser head and reliable delivery of liquid. The arrangement of the wick structure within the cannula can also be conducive to the advantageous retention of the heating element-wick structure assembly.

Preferably, the heating element-wick structure assembly is formed as a layered assembly to promote a compact design and smooth functioning. The layered assembly comprises the heating element and the wick structure, the wick structure being arranged at the inlet side of the heating element. The heating element and the wick structure each form at least one layer of the layered assembly. Advantageously, the heating element and wick structure are in planar contact with one another so that the layered assembly is particularly compact and sturdy and/or the liquid is delivered in a capillary manner. Advantageously, liquid can be delivered into the layered assembly by means of the wick structure via the inlet side, and vaporised by the heating element. The layered assembly can comprise a plurality of layers held together separably or inseparably. In turn, the heating element and/or the wick structure can comprise a plurality of layers. The layered assembly can comprise additional layers, for example for connecting the wick structure and heating element, for influencing the liquid transport and/or for mechanical stability.

It is advantageous for the cannula to have a sheath extending between an attachment side and a pricking side, the sheath encasing, in particular closing, the circumference of the heating element-wick structure assembly at least in part. The sheath has an inner surface and defines the liquid-conducting channel of the cannula.

Advantageously, the heating element-wick structure assembly contacts the sheath, it being possible for the heating element-wick structure assembly to abut the inner surface of the sheath at least in part. Advantageously, the heating element-wick structure assembly is in circumferential contact with the sheath so as to allow for controlled liquid transport. The cannula has a longitudinal axis extending between the attachment side and the pricking side. The sheath extends in parallel with the longitudinal axis in the manner of a tube or hollow cylinder.

Preferably, the piercing region is designed for piercing an external component, in particular a liquid reservoir, so as to provide a simple hydraulic or liquid-conduction connection to an external component, in particular a liquid reservoir or liquid tank.

Advantageously, the piercing region has a cutting edge for ensuring that the cannula penetrates, pierces or cuts into the liquid reservoir safely, reliably and cleanly. In one embodiment, the cannula has a spike in the piercing region. The cannula can also be blunt so as to reduce the risk of injury to the consumer.

Preferably, the support plate has a through-opening, in which the heating element-wick structure assembly and/or the cannula can be retained, the liquid being able to be delivered from the cannula to the heating element through the through-opening. By way of example, the heating element is arranged at least in part within the through-opening. In this case, the outlet side of the heating element is aligned with the support plate. In another example, the outlet side of the heating element protrudes out of the support plate.

Preferably, the heating element-wick structure assembly extends at least in part through the through-opening in the support plate so as to be able to retain the heating element-wick structure assembly in the support plate and allow the wick structure and/or the heating element, in particular the outlet side, to be aligned and/or arranged advantageously.

It is advantageous for the vaporiser head to comprise a locking member for locking in an external component, in particular in a liquid reservoir, so as to be able to connect the vaporiser head to the liquid reservoir to form a ready-to-use unit. By way of example, the locking member may be magnetic and comprise magnets. The locking member may be mechanical and comprise, for example, a clip, a latch member, a clamp, a brace, a spring, a thread and/or another mechanical locking member.

The consumers may be able to release the locking member in a non-destructive manner. In this embodiment, the consumer can separate the vaporiser head from the liquid reservoir without any damage, for example to be able to change and/or clean the vaporiser head. By way of example, the vaporiser head or removable vaporiser can be cleaned using an in particular alcohol-based solution or by pyrolysis, depending on how often the vaporiser head has been used and whether a flavour or active ingredient is being changed. Following cleaning, the vaporiser head can be connected to a new or different liquid reservoir.

The locking member may be unable to be released by the consumer so that a ready-to-use unit for the consumer may be assembled once, for example by the manufacturer.

Preferably, the cannula consists of metal so as to provide an effective, flavour-neutral and standardised embodiment of the vaporiser head.

Preferably, a mouthpiece can be or is attached to the vaporiser head, in particular to the support plate, to facilitate vaporiser head and/or mouthpiece handling and/or cleaning for the user. The vaporiser head may comprise a locking member for locking the mouthpiece in place. Advantageously, the cannula and/or the heating element-wick structure assembly can be arranged such that, in the ready-to-use state, the cannula and/or the heating element-wick structure assembly is/are sunk into the mouthpiece (in particular in its entirety) to prevent the cannula causing injuries and/or the heating element-wick structure assembly becoming dirty, for example.

Advantageously, the heating element is a microelectromechanical system (MEMS) and/or is silicon-based, to allow for standardised and efficient manufacture and to provide high vapour or aerosol quality.

Advantageously, a tank housing of the liquid reservoir is designed to be able to be punctured by a cannula in order to connect a liquid-tight liquid reservoir, which is closed before being punctured by the cannula, to the vaporiser head in a liquid-conducting manner and advantageously in a liquid-tight manner. Advantageously, before being connected to the vaporiser head, the liquid reservoir contains a liquid specified by the manufacturer so as to prevent abuse of the inhaler. Advantageously, the liquid reservoir is designed to be punctured by the cannula in a determinable piercing portion which can be associated with the cannula.

Advantageously, the liquid reservoir can have a seal, in particular in the region of the piercing portion, that allows the cannula to be removed following the piercing, the liquid reservoir being liquid-tight following the removal. In this embodiment, the consumer can separate the liquid reservoir from the vaporiser head, for example to use the liquid in the liquid reservoir at a later date and/or to clean the vaporiser head.

Preferably, the tank housing of the liquid container comprises a piercing seal for determining that the liquid reservoir has not been tampered with, for example before being pierced by the cannula. Advantageously, the piercing seal is designed to be destroyed when the cannula pierces the liquid container. Advantageously, the piercing seal indicates the authenticity of the liquid reservoir and in particular of the liquid therein containing the flavours and/or active ingredients. In one embodiment, the piercing seal may remain legible after being pierced by the cannula. By way of example, the piercing seal may be a logo, a number, a check digit, a scannable code, for example a barcode or 2D code, and/or other elements that can be read by humans and/or machines.

Preferably, the liquid reservoir is made at least in part of plastics material and/or metal, in particular aluminium, capable of being punctured by a cannula, so as to allow for simple construction and manufacture of the liquid reservoir. By way of example, the liquid reservoir can either be or comprise a plastics pouch. The piercing seal advantageously consists of a material that can be punctured by a cannula and which may be the same material as the rest of the tank housing or a different material. For example, the tank housing can be made of plastics material and the piercing seal comprises an aluminium cap, aluminium foil or a plastics film which can be pierced by the cannula attached to the vaporiser head. In one embodiment, the liquid reservoir is designed as a hollow cylinder, in particular made of a plastics material.

It is advantageous for the liquid reservoir to comprise a locking device for locking an external component, in particular a vaporiser head, in place, in particular by means of a rotational movement. Advantageously, the locking device of the liquid reservoir is designed to interact with the locking member of the vaporiser head such that the liquid reservoir and the vaporiser head can form a ready-to-use unit. Preferably, the locking establishes a liquid-tight connection between the liquid reservoir and the external component. In one embodiment, the locking device is associated with at least one seal or sealing element for liquid-tight sealing so that the external component is locked in place in a liquid-tight manner.

By way of example, the locking device may be magnetic and/or comprise magnets. The locking device may be mechanical and comprise, for example, a clip, a latch member, a clamp, a brace, a spring, a thread and/or another mechanical locking device.

The consumer may be able to release the locking device in a non-destructive manner. In this embodiment, the consumer can separate the vaporiser head from the liquid reservoir without any damage in order to change and/or clean the vaporiser head.

The locking device may be unable to be released by the consumer so that a ready-to-use unit for the consumer may be assembled once, for example by the manufacturer.

Advantageously, the vaporiser head can pierce the liquid reservoir by means of the cannula to produce a ready-to-use unit, so as to be able to produce the ready-to-use consumption unit, comprising at least the vaporiser head and the liquid reservoir, in a simple and safe manner. In one embodiment, the consumption unit can be inserted into the inhaler as a cartridge, for example into an opening in the inhaler intended for receiving the consumption unit, for example on the side of the inhaler housing.

Advantageously, the consumption unit has a mouthpiece so that the consumption unit can be handled advantageously by the user.

Advantageously, the support plate of the vaporiser head is attached to the mouthpiece. The consumer may be able to release the attachment of the vaporiser head to the mouthpiece in a non-destructive manner, or alternatively the attachment may be non-releasable. In one embodiment, the mouthpiece can form a part of the inhaler housing of the ready-for-operation inhaler.

Advantageously, in the ready-to-use state, the cannula is sunk into the mouthpiece, in particular in its entirety, so as to avoid a risk of injury to the consumer from the cannula. The mouthpiece may have a hollow-cylinder portion, within which the cannula is arranged. Preferably, the cannula is arranged along a longitudinal axis of the hollow-cylinder portion of the mouthpiece, the mouthpiece extending in the hollow-cylinder portion coaxially with a longitudinal axis of the cannula. The liquid reservoir is designed or dimensioned such as to be inserted into the hollow-cylinder portion of the mouthpiece and to be punctured by the cannula in the process. The term "cylindrical" is not restricted to a round cross section, but rather may include any suitable cross sections.

In the ready-to-use state, the support plate is preferably aligned with the tank housing of the liquid reservoir so that it can be easily fitted into an inhaler housing of an inhaler and/or so that a cartridge without problematic edges for the user can be provided.

In the ready-to-use state, the support plate advantageously closes the liquid tank in a liquid-tight manner so as to provide the consumer with a liquid-tight unit during use.

In the ready-to-use state, the support plate preferably supplements the tank housing of the liquid reservoir to form a complete and liquid-tight liquid tank so that the liquid reservoir can be provided as a liquid-tight unit after having been punctured by the cannula.

A simple and reliable method for producing the ready-to-use consumption unit for the inhaler comprises providing a vaporiser head, providing a liquid reservoir and piercing the tank housing of the liquid reservoir using the cannula of the vaporiser head.

Preferably, the method comprises locking the vaporiser head in place on the liquid reservoir, in particular by means of a rotational movement, for example in the manner of a bayonet lock, so as to complete the method by way of defined locking that the user can identify. Advantageously, the cannula of the vaporiser head pierces the tank housing of the liquid reservoir at the same time as the locking.

BRIEF DESCRIPTION OF THE FIGURES

The invention will be described below on the basis of preferred embodiments with reference to the accompanying drawings, in which.

DETAILED DESCRIPTION

Figure 1:
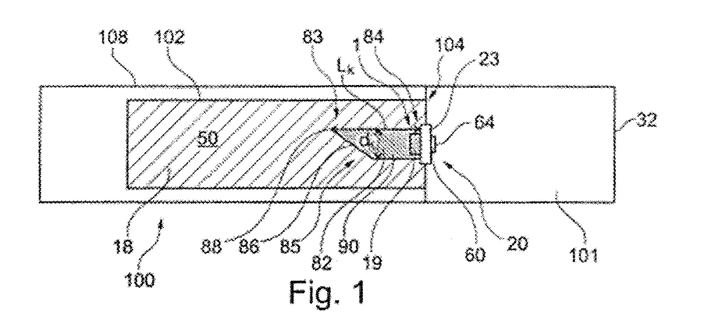
FIG. 1 is a schematic cross-sectional view of a consumption unit comprising a mouthpiece.
Figure 3:
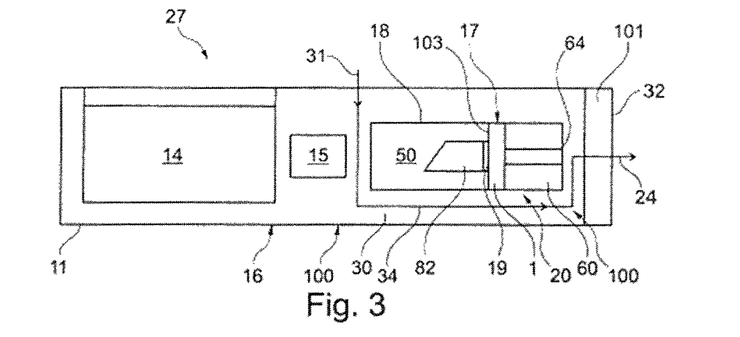
FIG. 3 is a schematic view of an inhaler.

FIG. 1 shows a ready-to-use consumption unit 100 for an inhaler 27 (shown for example in FIG. 3). The consumption unit 100 shown in FIG. 1 comprises a liquid reservoir 18, a vaporiser head 1 and a mouthpiece 101. The consumption unit 100 can form a removable cartridge 17. Advantageously, the user can replace the liquid reservoir 18 and/or reuse the vaporiser head 1 and/or the mouthpiece 101.

Figure 4:
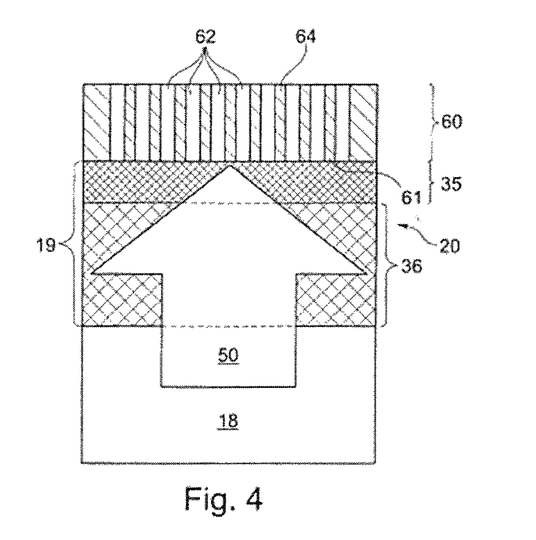
FIG. 4 is a schematic cross-sectional view of a layered assembly.
Figure 5:
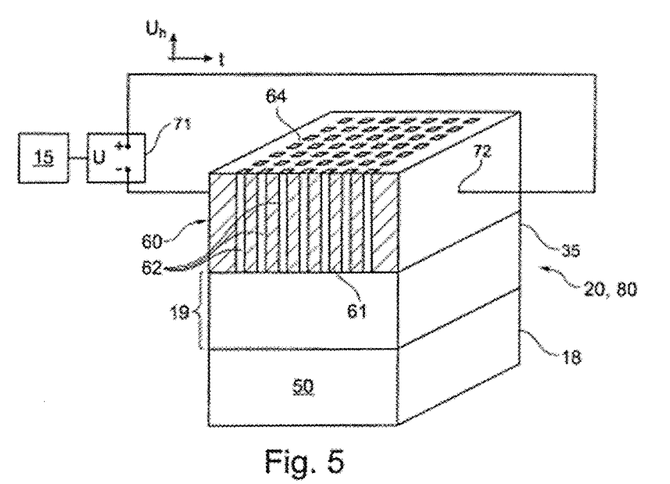
FIG. 5 is a perspective cross-sectional view of a layered assembly.
Figure 6:
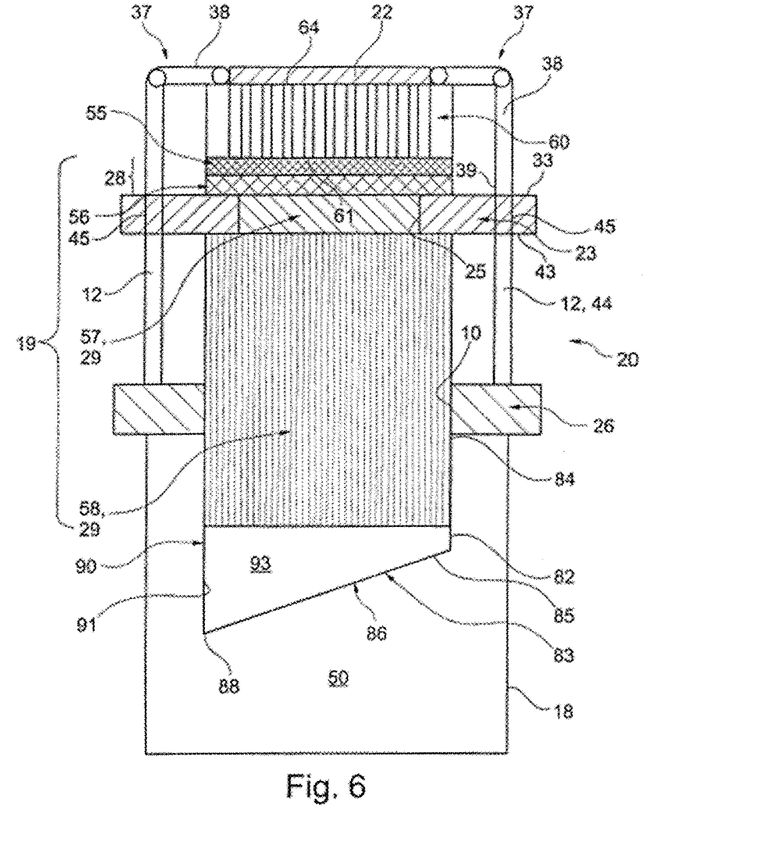
FIG. 6 is a schematic cross-sectional view of a layered assembly in one embodiment of the invention.

The vaporiser head 1 comprises a heating element-wick structure assembly 20 formed as a layered assembly and consisting of an electrically operable heating element 60 and a porous and/or capillary wick structure 19. Liquid 50 from the liquid reservoir 18 can be supplied to the heating element 60 by way of the wick structure 19. The heating element 60 is designed to vaporise the liquid 50 supplied to it, and to feed said liquid to an air stream 34 (FIG. 3) as an aerosol or vapour. The vaporiser head 1 comprises a support plate 23 for retaining the layered assembly 20, such that the support plate 23 and the layered assembly 20 are interconnected. FIGS. 4 to 6 each show example embodiments of a layered assembly 20.

The vaporiser head 1 in FIG. 1 has a liquid-conducting cannula 82, which is attached to the support plate 23 and/or to the heating element-wick structure assembly 20 at an attachment side 84 of the cannula 82.

Advantageously, the cannula 82 is tubular. A longitudinal axis is advantageously defined between a pricking side 85 and the attachment side 84. The sheath 90 advantageously extends in parallel and coaxially with the longitudinal axis over a length Lk. The sheath 90 defines a liquid-conducting channel 93 of the cannula 82 and has a circumference or diameter dk or another typical extension perpendicular to the longitudinal axis, for example an edge length.

Advantageously, the cannula 82 is elongate, i.e. the diameter dk is smaller than the length Lk along the longitudinal axis of the cannula 82. The external diameter dk of the cannula is advantageously between 0.25 mm and 3.4 mm, preferably between 0.5 mm and 1.8 mm. The length Lk of the cannula 82 is advantageously between 1 mm and 120 mm, preferably between 2 mm and 50 mm, more preferably between 3 mm and 10 mm. Advantageously, the cannula 82 is configured in the manner of a syringe cannula or injection cannula. In this example, the support plate 23 is planar and the cannula 82, in particular the longitudinal axis thereof, forms a right angle with the surface of the support plate 23.

At the pricking side 85, the cannula 82 advantageously comprises a piercing region 83, which may have a cutting edge 86 and/or a spike 88. Advantageously, the cutting edge 86 extends from an end, associated with the pricking side 85, of a tubular or hollow-cylindrical portion of the cannula 82 as far as to the spike 88 of the cannula 82. The spike 88 is designed to penetrate, pierce or cut into the liquid tank 50. Advantageously, the cutting edge 86 makes a defined cut into the liquid tank 50, the dimensions of the cut corresponding to the dimensions of the cannula 82, in particular to the thickness of the cannula 82.

The wick structure 19 and the heating element 60 are advantageously arranged at the attachment side 84. Advantageously, the cannula 82 encloses or encases the wick structure 19, i.e. the wick structure 19 is positioned at least in part in the channel 93 of the cannula 82. Advantageously, the heating element 60 is arranged at least in part outside the cannula 82, such that an outlet side 64 of the heating element 60 protrudes into the mouthpiece 101 shown in FIG. 1, where the air stream 34 can flow around it. The wick structure 19 extends from the attachment side 84, inside the cannula 82, along the longitudinal axis of the cannula 82, towards the pricking side 85.

The mouthpiece 101 and the layered assembly 20 are advantageously arranged such that, during proper use, the user cannot come into contact with the layered assembly 20 so as to protect the layered assembly 20 from becoming dirty and/or damaged.

The consumption unit 100 advantageously has a casing 108. The mouthpiece 101 preferably comprises the casing 108. In the ready-to-use state, the cannula 82 is advantageously sunk into the mouthpiece 101 or casing 108 in its entirety. The dimensions of the casing 108 are advantageously such that the liquid tank 50 can be inserted, for example slid and/or rotated, into the casing 108 so as to be punctured by the cannula 82.

Figure 2:
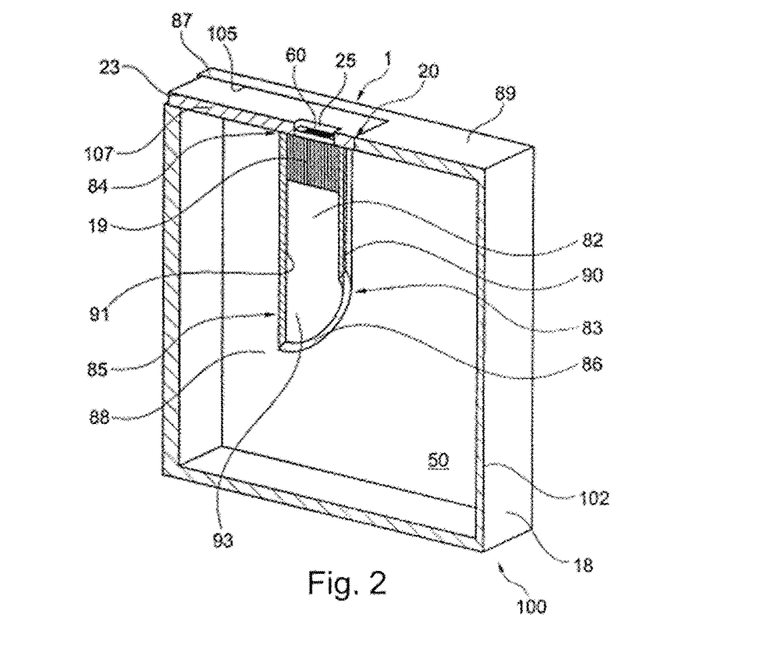
FIG. 2 is a perspective cross-sectional view of a consumption unit.

FIG. 2 shows a consumption unit 100, comprising a liquid reservoir 18 having a tank housing 102 and a vaporiser head 1. In this example, the locking device 105 comprises a recess 107 in the tank housing 102, for example in an end face 89 of the tank housing 102. The liquid reservoir 18 may have a piercing seal 103 in the region of the recess 107, said seal being designed to be punctured by the cannula 82. By way of example, the tank housing 102 can be made of a solid plastics material, unlike the piercing seal 103, and the piercing seal 103 can comprise a foil or cap capable of being punctured. In other embodiments, the tank housing 102 can also be a flexible pouch.

In the state shown in FIG. 2, the cannula 82 has pierced the liquid tank 18. The vaporiser head 1 is connected to the liquid reservoir 18 and/or locked in place by means of interacting locking members 87 and/or a locking device 105. Advantageously, a locking member 87 is arranged on the support plate 23. A locking device 105 interacting with the locking member 87 is advantageously arranged on the tank housing. The support plate 23 is advantageously designed such that the shape of the support plate 23 corresponds to the shape of the recess 107 in the tank housing 102. In the ready-to-use state, the support plate 23 is aligned with the tank housing 102 or the end face 89 of the tank housing 102 and closes the recess 107 in a liquid-tight manner.

Once the cannula 82 has pierced the liquid reservoir 18 and the vaporiser head 1 has been locked in place on the liquid tank 18, the support plate 23 and the tank housing 102 form a liquid-tight liquid tank 104.

Once the liquid reservoir 18 or liquid tank 104 has been emptied, it can be separated from the vaporiser head 1 using a locking member 87 that can be released in a non-destructive manner, the liquid reservoir 18 or liquid tank 104 being able to be disposed of and/or the vaporiser head 1 being able to be cleaned and reused, in particular multiple times. In this example, the liquid tank 18 is part of a removable cartridge 17 or forms a removable cartridge 17.

The liquid reservoir 18 or liquid tank 104 holds a liquid 50 containing flavours and/or active ingredients, in particular nicotine and/or medicinal substances. An advantageous volume of the liquid reservoir 18 is in the range between 0.1 ml and 5 ml, preferably between 0.5 ml and 3 ml, more preferably between 0.7 ml and 2 ml, or 1.5 ml. Preferably, the liquid reservoir 18 or liquid tank 104 is pre-filled, i.e. filled by the manufacturer of the liquid reservoir 18 or liquid tank 104.

FIG. 3 shows an inhaler 27 (in this case an electronic cigarette product) comprising an inhaler housing 11, in which an air channel 30 is provided between at least one air inlet opening 31 and an air outlet opening 24 at a mouth end 32 of the inhaler 27. In this respect, the mouth end 32 of the inhaler 27 refers to the end at which the consumer draws in breath for inhalation purposes, thereby generating negative pressure in the inhaler 27 and producing an air stream 34 in the air channel 30.

Advantageously, the inhaler 27 consists of a reusable basic part 16 and a consumption unit 100. The consumption unit 100 comprises the vaporiser head 1 and the liquid reservoir 18.

In one embodiment, the ready-to-use unit consisting of the vaporiser head 1 and liquid reservoir 18 can be inserted into the mouthpiece 101 in the manner of a cartridge. The consumption unit 100 thus formed consisting of the cartridge and mouthpiece 101 can then be connected to the basic part 16 to form the ready-to-use inhaler 27.

In another embodiment, the mouthpiece 101 is connected to the vaporiser head 1 in a non-detachable manner for the consumer. In this embodiment, the liquid reservoir 18 is inserted into the mouthpiece 101, whereby the cannula 82 penetrates the liquid reservoir 18. The consumption unit 100 thus formed consisting of the mouthpiece 101 together with the vaporiser head 1 and liquid reservoir can then in turn be connected to the basic part 16 to form the ready-to-use inhaler 27.

The mouthpiece 101 can form part of the inhaler housing 11 of the ready-to-use inhaler 27 or supplement the inhaler housing 11.

In one embodiment, the consumption unit 100 can be inserted into the inhaler housing 11 and fixed in place therein as a ready-to-use cartridge or removable cartridge 17, for example into an opening in the inhaler housing 11 for example on a side of the inhaler 27.

In the air channel 30, the air sucked in through the inlet opening 31 is conducted towards or along at least one layered assembly 20. The layered assembly 20 is or can be connected to at least one liquid reservoir 18, in which at least one liquid 50 is stored. The layered assembly 20 vaporises liquid 50 supplied thereto from the liquid reservoir 18 and feeds the vaporised liquid into the air stream 34 at an outlet side 64 as an aerosol/vapour 22 (see FIG. 6). In one embodiment, the air supply flowing past the layered assembly 20 or vaporiser towards the mouthpiece 101 is advantageously ensured by the entire inhaler housing 11.

The inhaler 27 further comprises an electrical energy storage device 14 and an electronic controller 15. The energy storage device 14 is generally arranged in the basic part 16 and can in particular be an electrochemical single-use battery or a rechargeable electrochemical accumulator, for example a lithium ion accumulator. The electronic controller 15 comprises at least one digital data processing device, in particular a microprocessor and/or microcontroller, in the basic part 16 (as shown in FIG. 3) and/or in the consumption unit 17.

Advantageously, a sensor, for example a pressure sensor or a pressure or flow switch, is arranged in the inhaler housing 11, the controller 15 being able to determine on the basis of a sensor signal output by the sensor whether a consumer is drawing in breath for inhalation purposes at the mouth end 32 of the cigarette product 10. In this case, the controller 15 actuates the layered assembly 20 to feed liquid 50 from the liquid reservoir 18 into the air stream 34 as an aerosol/vapour.

The liquid 50 stored in the liquid reservoir 18 and to be metered in is, for example, a mixture of 1,2-propylene glycol, glycerol, water, at least one flavour and/or at least one active ingredient, in particular nicotine and/or therapeutic active ingredients.

Advantageously, the consumption unit 100 comprises a non-volatile data memory for storing information or parameters relating to the consumption unit 100. The data memory can be part of the electronic controller 15. Advantageously, the data memory stores information on the composition of the liquid 50 stored in the liquid reservoir 18; information on the process profile, in particular power/temperature control; data on status monitoring or system checks, for example tightness checks; data on copying protection and protection against forgery; an ID for clearly identifying the consumption unit 100; serial numbers; the date of manufacture and/or expiry; and/or inhalation number (the number of times the consumer has inhaled) or usage time. Advantageously, the data memory is or can be connected to the controller 15 by means of contacts and/or lines.

FIGS. 4 and 5 show an advantageous embodiment of a vaporiser unit or a heating element-wick structure assembly 20 formed as a layered assembly. The vaporiser unit or layered assembly 20 comprises a block-like, preferably monolithic, heating element 60, preferably made of an electrically conductive material, preferably doped silicon, doped ceramics, metal-ceramics, filter ceramics, semiconductors, in particular germanium, graphite, metalloid and/or metal. It is not necessary for the entire heating element 60 to be made of an electrically conductive material. It may be sufficient, for example, for the surface of the heating element 60 to be coated with an electrically conductive material, for example a metal material. In this case, the entire surface need not be coated; for example, conducting tracks can be provided on a non-conductive main body. It is also not strictly necessary for the entire heating element 60 to heat up; it may be sufficient, for example, for a portion or a heating layer of the heating element 60 to heat up in the region of the output side 64.

The heating element 60 is provided with a plurality of microchannels or through-channels 62, which connect an inlet side 61 of the heating element 60 to an outlet side 64 in a liquid-conducting manner. The inlet side 61 is connected to the liquid reservoir 18 in a liquid-conducting manner by means of a wick structure 19. The wick structure 19 is used for passively delivering liquid from a liquid reservoir 50 to the heating element 60 by means of capillary forces.

The average diameter of the through-channels 62 is preferably in the range between 5 μm and 200 μm, more preferably in the range between 30 μm and 150 μm, even more preferably in the range between 50 μm and 100 μm. Due to these dimensions, a capillary effect is advantageously produced such that liquid penetrating a through-channel 62 at the inlet side 61 rises upwards through the through-channel 62 until the through-channel 62 is filled with liquid. The volume ratio of through-channels 62 to heating element 60, which can be referred to as the porosity of the heating element 60, is in the range, for example, between 10% and 50%, advantageously in the range between 15% and 40%, even more advantageously in the range between 20% and 30%, and is for example 25%.

In an embodiment that has not been shown, the edge lengths and/or the diameter of the surfaces of the heating element 60 that are provided with the through-channels 62 are, for example, in the range between 0.5 mm and 3 mm, preferably between 0.5 mm and 1 mm.

The dimensions of the surfaces of the heating element 60 that are provided with through-channels 62 can be, for example, 0.95 mm×1.75 mm, 1.9 mm×1.75 mm or 1.9 mm×0.75 mm. In an embodiment that has not been shown, the edge lengths and/or the diameter of the heating element 60 can, for example, be in the range between 0.5 mm and 5 mm, preferably in the range between 0.75 mm and 4 mm, more preferably in the range between 1 mm and 3 mm. The surface (chip size) of the heating element 60 can, for example, measure 1 mm×3 mm, 2 mm×2 mm or 2 mm×3 mm.

The width or diameter of the heating element 60 is preferably in the range between 1 mm and 5 mm, more preferably in the range between 2 mm and 4 mm, and is for example 3 mm. The height of the heating element 60 is preferably in the range between 0.05 mm and 1 mm, more preferably in the range between 0.1 mm and 0.75 mm, even more preferably in the range between 0.2 mm and 0.5 mm, and is for example 0.3 mm.

The number of through-channels 62 is preferably in the range between 4 and 1000. In this way, the heat input from the substrate into the through-channels 62 can be optimised, and an assured high vaporisation power and a sufficiently large vapour output surface area can be achieved.

The through-channels 62 are arranged in the form of a square, rectangular, polygonal, round, oval or other shape array, as can be seen in FIG. 5. The array can be in the form of a matrix having s columns and z rows, s advantageously being in the range between 2 and 50 and more advantageously in the range between 3 and 30 and/or z advantageously being in the range between 2 and 50 and more advantageously in the range between 3 and 30. In this way, an effective and simple-to-produce arrangement of the through-channels 62 can be produced in which high vaporisation power is ensured.

The cross section of the through-channels 62 can be square, rectangular, polygonal, round, oval or another shape, and/or can change in portions, in particular increase or decrease, or remain constant in the longitudinal direction.

The length of one or each through-channel 62 is preferably in the range between 100 μm and 1000 μm, more preferably in the range between 150 μm and 750 μm, even more preferably in the range between 180 μm and 400 μm, and is for example 300 μm. In this way, optimum liquid uptake and portion formation can be achieved while at the same time having sufficiently good heat input from the heating element 60 into the through-channels 62.

The distance between two through-channels 62 is preferably at least 1.3 times the clear diameter of a through-channel 62, the distance being based on the central axes of the two through-channels 62. The distance can preferably be 1.5 to 5 times, more preferably 2 to 4 times, the clear diameter of a through-channel 62. In this way, optimum heat input from the substrate into the through-channels and a sufficiently sturdy arrangement and wall strength of the through-channels can be achieved.

On the basis of the above-described features, the heating element 60 can also be referred to as a volume heater.

The layered assembly 20 has a heating voltage source 71, which can preferably be controlled by the controller 15 and is connected to the heating element 60 by means of electrodes 72 on opposite sides thereof, such that an electrical voltage Uh generated by the heating voltage source 71 leads to a current flow through the heating element 60. Owing to the ohmic resistance of the electrically conductive heating element 60, the current flow causes the heating element 60 to heat up and thus the liquid contained in the through-channels 62 to vaporise. The heating element 60 thus acts as a vaporiser. Vapour/aerosol generated in this manner escapes from the through-channels 62 towards the outlet side 64 and is mixed with the air stream 34 (see FIG. 3). More precisely, when the controller 15 detects an air stream 34 through the air channel 30 caused by the consumer drawing in breath, it actuates the heating voltage source 71, in which case the liquid located in the through-channels 62 is driven out of the through-channels 62 in the form of vapour/aerosol due to spontaneous heating.

In the process, in the event of different temperatures and/or if the individual components of the individual portions of the liquid are vaporised, the duration of the individual vaporisation steps can be kept short and/or can be clocked at an actuation frequency such that the consumer is unaware of the gradual vaporisation and yet a largely homogeneous aerosol formation can be ensured with no effect on taste and in a reproducibly precise manner. In particular, a component of the liquid having a low boiling point is vaporised first in a first vaporisation period at a first temperature A, and then a component of the liquid having a higher boiling point is vaporised in a second vaporisation period at a second temperature B, which is higher than the temperature A.

Preferably, a voltage curve Uh(t) adapted to the liquid mixture being used is stored in the data memory of the inhaler 10 (see FIG. 5). This makes it possible to specify the voltage curve Uh(t) of the used liquid in an adapted manner, such that the heating temperature of the heating element 60, and thus also the temperature of the capillary through-channels 62, can be controlled over time during the vaporisation process in accordance with the known vaporisation kinetics of the particular liquid, thereby ensuring optimum vaporisation results. The vaporisation temperature is, for example, in the range between 100° C. and 400° C., preferably between 150° C. and 350° C., more preferably between 190° C. and 290° C. In some applications, for example medical applications, a vaporisation temperature of less than 100° C. can be provided in order to administer proteins and/or active ingredients without damaging them.

At the inlet side 61 of the heating element 60, a porous and/or capillary liquid-conducting wick structure 19 is arranged. The wick structure 19 contacts the inlet side 61 of the heating element 60 in a planar manner and covers all the through-channels 62 on the inlet side, as can be seen in FIGS. 4 and 5. At the side opposite the heating element 60, the wick structure 19 is connected to the liquid reservoir in a liquid-conducting manner. The direct connection of the liquid reservoir 18 to the wick structure 19 should only be taken as an example. In particular, a liquid interface and/or a plurality of liquid lines may be provided between the liquid reservoir 18 and the wick structure 19. Therefore, the liquid reservoir 18 can also be arranged at a distance from the wick structure 19. The dimensions of the liquid reservoir 18 can be larger than those of the wick structure 19 (see FIG. 6, for example). By way of example, the wick structure 19 can be inserted into an opening in a tank housing 102 of the liquid reservoir 18. A plurality of layered assemblies 20 can also be associated with one liquid reservoir 18.

The wick structure 19 consists of porous and/or capillary material, which, due to capillary forces, is able to passively deliver sufficient amounts of liquid vaporised by the heating element 60 from the liquid reservoir 18 to the heating element 60 so as to prevent the through-channels 62 running dry and the problems associated therewith.

The wick structure 19 advantageously consists of a non-conductive material to prevent undesirable heating of liquid in the wick structure 19 as a result of the current flow. The wick structure 19 advantageously consists of one or more of the materials cotton, cellulose, acetate, glass cloth, glass fibre ceramics, sintered ceramics, ceramic paper, alumino-silicate paper, metal foam, metal sponge, another heat-resistant, porous and/or capillary material having a sufficient delivery rate, or a composite of two or more of the aforementioned materials. In an advantageous practical embodiment, the wick structure 19 can comprise at least one ceramic fibre paper and/or a porous ceramic. The volume of the wick structure 19 is preferably in the range between 1 mm³ and 10 mm³, more preferably in the range between 2 mm³ and 8 mm³, even more preferably in the range between 3 mm³ and 7 mm³, and is for example 5 mm³.

If the wick structure 19 consists of a conductive material, which is not ruled out, an insulation layer that is made of an electrically and/or thermally insulating material, for example glass, ceramics or plastics material, and has through-openings corresponding to the through-channels 62 and extending through the insulation layer, is advantageously provided between the wick structure 19 and the heating element 60.

The size of the pores or capillaries in the material of the wick structure 19 is subject to advantageously determined parameters. For example, the average pore/capillary size Dw of pores or capillaries of the wick structure 19 in the contact region 35, 61 with the heating element 60 is advantageously minimal, i.e. Dw=Pmin, and/or is advantageously smaller than the smallest distance Dp between two through-channels 62, preferably by at least a factor of 2, more preferably by at least a factor of 5, i.e. Dw«Dp. In addition, the average pore/capillary size Dw of pores or capillaries of the wick structure 19 in the contact region 35, 61 with the heating element 60 is advantageously smaller than the smallest clear diameter Dpw of a through-channel 62, preferably by at least a factor of 2, more preferably by at least a factor of 5, i.e. Dw«Dpw.

The wick structure 19 in the contact region 35, 61 with the heating element 60 is used to uniformly distribute liquid, to be temperature-resistant and to form a type of stop valve by means of its relatively small pores and/or thin capillaries, so as to prevent bubble-containing liquid flowing back in an undesirable manner out of the heating element 60 into the wick structure 19 and/or into the liquid reservoir 18.

In the embodiment according to FIG. 4, the wick structure 19 has two, for example planar, layers 35, 36, specifically one wick layer 35 abutting the inlet side 61 of the heating element 60 in a planar manner and contacting said side, said layer being referred to as a contact layer, and an adjoining wick layer 36, which is connected to the liquid reservoir 18 in a liquid-conducting manner and can be referred to as the more remote wick layer.

The contact layer 35 has a substantially constant pore/capillary size distribution and a substantially constant average pore/capillary size Dw that is significantly smaller than the smallest distance Dp between two through-channels 62 and significantly smaller than the smallest clear diameter Dpw of a through-channel 62: Dw«Dp, Dpw.

The more remote wick layer 36 has a substantially constant pore/capillary size distribution and a substantially constant average pore capillary size Dw' that is significantly larger than the average pore/capillary size Dw of the contact layer 35: Dw'>Dw, but preferably still smaller than Dp and/or Dpw: Dw'<Dp, Dpw.

In an advantageous practical embodiment, the contact layer 35 can be, for example, a fibre paper or ceramic paper layer and/or the layer 36 can be a porous ceramic.

It goes without saying that the wick structure 19 can have more than two wick layers 35, 36, etc. Even when there are more than two wick layers, 35, 36, etc., the average pore/capillary size decreases, advantageously monotonically (i.e. from wick layer to wick layer), as the distance from the heating element 60 decreases, and/or remains the same, i.e. does not increase in any case.

In the embodiment according to FIG. 5, the wick structure 19 consists of just one layer, the average pore/capillary size of which decreases monotonically as the distance from the heating element 60 decreases.

In all the embodiments, the desired pore/capillary size gradient can be set optimally and the liquid flow towards the heating element 60 can be slowed and homogenised.

The above-described reduction in the average pore/capillary size in the wick structure 19 as the distance from the heating element 60 decreases applies in the direction perpendicular to the inlet side 61 of the heating element, i.e. perpendicularly to the contact surface between the heating element 60 and the wick structure 19, or in parallel with the course of the through-channels 62. However, within one view with the same distance d from the heating element 60, the average pore/capillary size in the wick structure 19 is advantageously constant so that all the through-channels 62 of the heating element 60 are supplied with liquid uniformly.

The through-channels 62 are preferably arranged having their longitudinal axis transverse to the layers 19, 35, 36 or, more generally, to any layer sequence. In this way, optimum heat input from the heating element 60 into the through-channels 62 can be achieved.

The heating element 60 can advantageously be produced using thin-film coating technology from segments of a wafer that has a layer thickness of preferably less than or equal to 1000 μm, more preferably 750 μm, even more preferably less than or equal to 500 μm and advantageously 300 μm. Surfaces of the heating element 60 can advantageously be hydrophilic. Advantageously, the inlet side 61 and/or the outlet side 64 of the heating element 60 can be microstructured or have microgrooves.

The heating element-wick structure assembly 20 is adjusted such that a volume of liquid preferably in the range between 1 μl and 20 μl, more preferably between 2 μl and 10 μl, even more preferably between 3 μl and 5 μl, typically 4 μl, is metered in per breath drawn in by the consumer. Preferably, the heating element-wick structure assembly 20 can be adjusted in terms of the liquid/vapour volume per breath, i.e. depending on the inhalation duration from 0.5 s to 5 s, preferably from 1 s to 3 s.

In the embodiment according to FIG. 6, the wick structure 19 comprises more than two layers, in this case four layers. Directly adjacent to the heating element 60, and in planar contact therewith, there is a filter layer 55, which can consist in particular of one, two or more glass microfibre layers. Adjoining this layer, a fibre paper layer 56 can be arranged in a planar manner. Advantageously, wick layers 57, 58, for example a ceramic wick layer 57 and an oil lamp wick layer 58, i.e. a glass fibre wick material conventionally used for oil lamp wicks, are provided adjoining said fibre paper layer in a planar manner.

In the embodiment according to FIG. 6, at least the layer 55 abutting the heating element 60 in a planar manner advantageously fulfils the aforementioned conditions for the pore/capillary size Dw«Dp, Dpw. Advantageously, the layer 57 and/or the layer 58 can also fulfil these conditions. In addition, the capillary forces for the capillary delivery of the liquid from the liquid reservoir 18 to the heating element 60 can be provided largely or entirely by the wick layers 57, 58. Generally, it is not necessary for all the layers of the wick structure 19 to provide capillary forces for the capillary delivery of the liquid. It may also be sufficient for just one layer of the wick structure 19 to provide capillary forces for the capillary delivery of the liquid.

Figure 7:
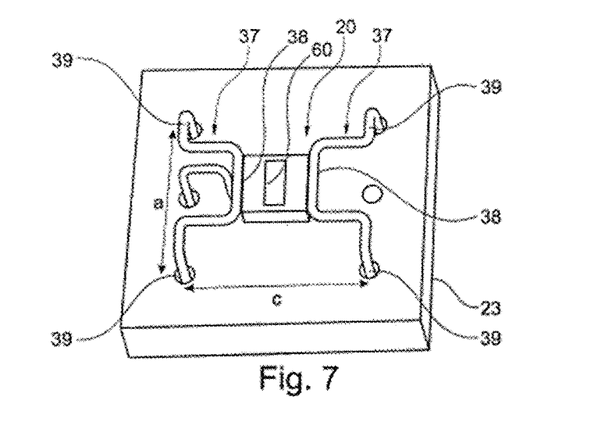
FIGS. 7 and 8 are perspective views of a support plate from the side of a heating element or from the side opposite a liquid supply.
Figure 8:
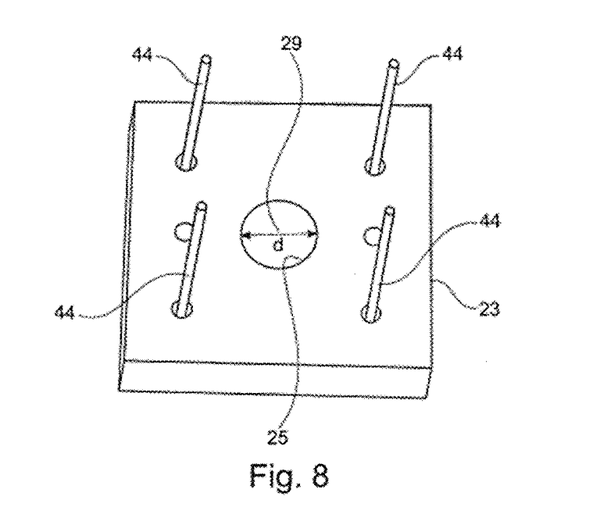

The heating element-wick structure assembly 20 advantageously has an, in particular plate-like, support 23 for retaining the heating element 60 and/or the wick structure 19, as shown in FIG. 6 to 8. The support 23 can consist of a suitable material, for example ceramics, glass and/or plastics material, including fibre-reinforced plastics material, for example printed circuit board material, and has a through-opening 25, through which the wick structure 19 extends and in which the wick structure 19 is retained.

The thickness of the support 23 is preferably in the range between 0.5 mm and 4 mm, more preferably in the range between 1 mm and 3 mm, even more preferably in the range between 1 mm and 2 mm, and can be 1.6 mm or 2 mm, for example. The thickness of a wick layer 57 arranged in the through-opening 25 in the support 23 can be adapted to the thickness of the support 23 or can correspond thereto and thus also be 1.6 mm or 2 mm, for example.

The through-opening 25 is advantageously circular, which is simple to produce. The diameter d, or optionally the average diameter, of the through-opening 25 (see FIG. 8) is preferably in the range between 0.5 mm and 4 mm, preferably in the range between 1 mm and 3 mm, more preferably in the range between 1.5 mm and 2.5 mm, and is for example 2 mm.

The diameter d of the through-opening 25 is smaller than or equal to, advantageously smaller than, the width or diameter b of the heating element 60 (see FIG. 8). The volume of the through-opening 25 or the wick volume in the through-opening 25 is advantageously in the range between 1 $mm^3$ and 8 $mm^3$, preferably in the range between 2 $mm^3$ and 6.5 $mm^3$, more preferably in the range between 2.5 $mm^3$ and 5 $mm^3$.

When in the free, pre-assembled state, the wick structure 19 may be oversized, i.e. may have a greater diameter than the through-opening 25, so as to generate additional retaining forces for the shaft 29 in the through-opening 25.

The diameter of the wick layer 35 is advantageously greater than the diameter d of the through-opening 25. Preferably, around its entire circumference the wick layer 35 protrudes beyond the through-opening 25 by a protruding length. Owing to the all-round protruding length of the wick layer 35 beyond the through-opening 25, when the heating element 60 is clamped on the support 23, the wick layer 35 and thus the entire wick structure 19 is securely retained in the heating element-wick structure assembly 20.

The heating element 60 is clamped on the support 23 by means of at least two clamping members 37 (see in particular FIG. 7), which grip said heating element 60 on opposite sides thereof. Each clamping member 37 advantageously has a clamping bracket 38, which is attached to the support 23 in a resilient manner at two spaced-apart attachment points 39 and generates a pretension, by which the heating element 60 and the disc 28 are rigidly clamped on the support 23 and thus securely retained.

The distance a between the two attachment points 39 of a clamping bracket 38 is preferably in the range between 4 mm and 10 mm, more preferably in the range between 5 mm and 8 mm, and is for example 6 mm. The distance c between the attachment points 39 of two clamping brackets 39 is preferably in the range between 5 mm and 12 mm, more preferably in the range between 6 mm and 10 mm, and is for example 8 mm. The dimensions of the (for example) rectangular support 23 are preferably in the range between 6 mm and 20 mm, more preferably in the range between 8 mm and 17 mm, and even more preferably in the range between 10 mm and 14 mm.

Particularly advantageously, the clamping members 37 are used simultaneously as electrodes for contacting the heating element 60 and supplying the heating current thereto. For this purpose, the clamping members 37 or the clamping brackets 38 advantageously consist of an electrically conductive material, for example a metal wire, e.g. brass wire. The linear contact between the clamping bracket 38 and the heating element 60 produces an excellent electrical connection between the clamping member 37 and the heating element 60 while at the same time having ideal thermal decoupling between the clamping member 37 and the heating element 60 due to a lack of full-surface contact. As a result, heat dissipation from the heating element 60 into the clamping member 37 is low and the electrodes 38 remain significantly cooler than the heating element 60.

Diode effects are prevented and purely ohmic charge carrier transport is ensured.

The clamping bracket 38 can clamp the heating element 60 to the side in parallel with the outlet side 64 and/or perpendicularly to the outlet side 64 and/or in a corner groove having an intermediate angle, for example between 30° and 60°, both to the side and perpendicularly to the outlet side 64. The last-mentioned possibility involves two contact lines between the clamping bracket and the heating element 60, thereby further improving the electrical contact. A clamping member 37 can also have more than one clamping bracket 38, in particular any two or all three clamping brackets.

By means of electrical lines 12, the clamping members 37 are advantageously connected to a printed circuit board 26 (PCB) provided in the consumption unit 17 in order to establish the electrical connection to the electronic controller 15 and to the energy source 46 for supplying power to the heating element 60. Electronic components of the consumption unit 17 are advantageously arranged on the printed circuit board 26.

In the embodiment according to FIG. 6, the printed circuit board 26 is a separate part and is arranged at a distance from the support 23 on the side 43 thereof facing away from the heating element 60. The printed circuit board 26 has a through-opening 10, through which the wick structure 19 extends and in which the wick structure 19 is retained. In this case, the electrical lines 12 comprise four metal pins 44, for example, which are connected to the clamping members 37 in the attachment points 39 on the side 33 of the support 23 and are each guided through the support 23 through a through-hole 45 and then bridge the gap between the support 23 and the printed circuit board 26 on the side 43 facing away therefrom.

In another embodiment, the support 23 can form the printed circuit board 26. The electrical lines 12 can then be omitted. It is also possible for the heating element-wick structure assembly 20 to not even comprise a printed circuit board, but rather for the clamping bracket 38 to be connected to a printed circuit board, arranged for example in the basic part 16, by means of flexible insulated lines 12, for example, or in another suitable manner.

On the underside 43 of the support 23, a sealing element 73, for example a sealing ring, can be arranged for sealing the support 23 with respect to a housing of the liquid reservoir 18 or of another component arranged below the support 23.

FIG. 6 shows a cannula 82, through which the wick structure 19, in particular the wick layer 58 or the shaft 29, extends. In this example, the cannula 82 is retained by the printed circuit board 26, for example by the cannula 82 being clamped into the through-opening 10 by a portion of the sheath 90, said portion being arranged on the attachment side 84.

The wick layer 58 is in circumferential contact with the inner surface 91 of the sheath 90 and extends through the channel 93 of the cannula 82.

The sequence of the vaporisation process will be explained below.

In an initial state, the voltage source 71 for the heating process is switched off.

To vaporise liquid 50, the voltage source 71 for the heating element 60 is activated. In the process, the voltage Uh is set such that the vaporisation temperature in the heating element 60 and thus in the through-channels 62 is adapted to the specific vaporisation behaviour of the liquid mixture used. This prevents the risk of local overheating and thus the formation of toxins.

As soon as a volume of liquid corresponding to or correlated with the volume of the through-channels 62 has been vaporised, the heating voltage source 71 is deactivated. Since, advantageously, the precise liquid properties and volume are known and the heating element 60 has a measurable temperature-dependent resistance, said time can be determined or controlled very precisely. The energy consumption of the heating element-wick structure assembly 20 can thus be reduced compared with known apparatuses since the required vaporisation energy can be introduced in a metered manner and thus more precisely.

After the end of the heating process, the through-channels 62 are largely or entirely empty. The heating voltage 71 is then kept switched off until the through-channels 62 are refilled by means of liquid being subsequently delivered through the wick structure 19. As soon as this has occurred, the next heating cycle can be started by switching on the heating voltage 71.

Advantageously, the actuation frequency of the heating element 60, said frequency being generated by the heating voltage source 71, is generally in the range of 1 Hz to 50 kHz, preferably in the range from 30 Hz to 30 kHz, even more advantageously in the range between 100 Hz and 25 kHz.

The frequency and duty cycle of the heating voltage Uh for the heating element 60 are advantageously adapted to the inherent oscillation or inherent frequency of the bubble oscillations during bubble boiling. Advantageously, the period duration 1/f of the heating voltage can thus be in the range between 1 ms and 50 ms, more advantageously between 10 ms and 40 ms, even more advantageously between 15 ms and 30 ms, and can be for example 20 ms. Depending on the composition of the vaporised liquid, frequencies other than those mentioned can optimally be adapted to the inherent oscillation or inherent frequency of the bubble oscillations.

In addition, it has been found that the maximum heating current generated by the heating voltage Uh should preferably be no more than 7 A, more preferably no more than 6.5 A, even more preferably no more than 6 A, and optimally should be in the range between 2 A and 6 A so as to ensure concentrated vapour while avoiding overheating. The heating current may have a lower limit of for example 1 A, preferably 2 A, so as to ensure sufficient vaporisation.

In turn, the delivery rate of the wick structure 19 is optimally adapted to the vaporisation rate of the heating element 60 such that sufficient liquid can be subsequently delivered at any time and that the region upstream of the heating element 60 can be prevented from running dry.

The heating element-wick structure assembly 20 is preferably based on MEMS technology, in particular made of doped silicon, and therefore is advantageously a microelectromechanical system.

In accordance with the above, what is advantageously proposed is a heating element-wick structure assembly 20 consisting of a silicon-based heating element 60, which is advantageously planar at least on the inlet side 61, and one or more capillary structures 19 therebelow, which advantageously have different pore sizes. The wick structure 19 arranged directly at the inlet side 61 of the heating element 60 prevents the formation of bubbles at the inlet side 61 of the heating element 60 since gas bubbles obstruct any further delivery action and simultaneously lead to (local) overheating of the heating element 60 due to a lack of cooling from subsequently flowing liquid.

EMBODIMENTS

Embodiment 1

Vaporiser head (1) for an inhaler (27), in particular for an electronic cigarette product, comprising:
a heating element-wick structure assembly (20) having an electrically operable heating element (60), which has at least one liquid-conducting through-channel (62) and a porous and/or capillary wick structure (19) arranged at an inlet side (61) of the heating element (60), and
a support plate (23) for retaining the heating element-wick structure assembly (20), characterised in that
the vaporiser head (1) has a liquid-conducting cannula (82) having a preferably protruding piercing region (83).

Embodiment 2

Vaporiser head (1) according to embodiment 1, characterised in that
the wick structure (19) and/or the heating element (60) is/are arranged on an attachment side (84) of the cannula (82).

Embodiment 3

Vaporiser head (1) according to any of the preceding embodiments, characterised in that
the wick structure (19) is arranged at least in part inside the cannula (82).

Embodiment 4

Vaporiser head (1) according to any of the preceding embodiments, characterised in that
the heating element-wick structure assembly (20) is formed as a layered assembly.

Embodiment 5

Vaporiser head (1) according to any of the preceding embodiments, characterised in that
the cannula (82) has a sheath (90) extending between an attachment side (84) and a pricking side (85),
the sheath (90) circumferentially encasing, in particular closing, the heating element-wick structure assembly (20) at least in part.

Embodiment 6

Vaporiser head (1) according to any of the preceding embodiments, characterised in that the piercing region (83) is designed for piercing an external component, in particular a liquid reservoir (18).

Embodiment 7

Vaporiser head (1) according to any of the preceding embodiments, characterised in that
the piercing region (83) has a cutting edge (86).

Embodiment 8

Vaporiser head (1) according to any of the preceding embodiments, characterised in that
the support plate (23) has a through-opening (25).

Embodiment 9

Vaporiser head (1) according to embodiment 8, characterised in that
the heating element-wick structure assembly (20) extends at least in part through the through-opening (25) in the support plate (23).

Embodiment 10

Vaporiser head (1) according to any of the preceding embodiments, characterised in that
the vaporiser head (1) comprises a locking member (87) for locking in an external component, in particular in a liquid reservoir (18).

Embodiment 11

Vaporiser head (1) according to any of the preceding embodiments, characterised in that
a mouthpiece (101) can be attached to the vaporiser head (1), in particular to the support plate (23).

Embodiment 12

Vaporiser head (1) according to any of the preceding embodiments, characterised in that
the cannula (82) consists of metal.

Embodiment 13

Vaporiser head (1) according to any of the preceding embodiments, characterised in that
the heating element (60) is a microelectromechanical system (MEMS) and/or is silicon-based.

Embodiment 14

Liquid reservoir (18) comprising a tank housing (102), characterised in that
the tank housing (102) can be punctured by a cannula (82).

Embodiment 15

Liquid reservoir (18) according to embodiment 14, characterised in that
the tank housing (102) of the liquid reservoir (18) comprises a piercing seal (103).

Embodiment 16

Liquid reservoir (18) according to either embodiment 14 or embodiment 15, characterised in that
the liquid reservoir (18) is made at least in part of plastics material and/or metal, in particular aluminium, capable of being punctured by a cannula (82).

Embodiment 17

Liquid reservoir (18) according to any of embodiments 14 to 16, characterised in that
the liquid reservoir (18) comprises a locking device (105) for locking an external component, in particular a vaporiser head (1), in place, in particular by means of a rotational movement.

Embodiment 18

Consumption unit (100) comprising a vaporiser head (1) according to any of embodiments 1 to 13 and a liquid reservoir (18) according to any of embodiments 14 to 17, characterised in that
the vaporiser head (1) can pierce the liquid reservoir (18) by means of the cannula (82) to produce a ready-to-use consumption unit (100).

Embodiment 19

Consumption unit (100) according to embodiment 18, characterised in that the consumption unit (100) has a mouthpiece (101).

Embodiment 20

Consumption unit (100) according to embodiment 19, characterised in that
the support plate (23) of the vaporiser head (1) is attached to the mouthpiece (101).

Embodiment 21

Consumption unit (100) according to any of embodiments 18 to 20, characterised in that
in the ready-to-use state, the cannula (82) is sunk into the mouthpiece (101).

Embodiment 22

Consumption unit (100) according to any of embodiments 18 to 21, characterised in that
in the ready-to-use state, the support plate (23) is aligned with the tank housing (102) of the liquid reservoir (18).

Embodiment 23

Consumption unit (100) according to any of embodiments 18 to 22, characterised in that
in the ready-to-use state, the vaporiser head (1) closes the liquid tank (104) in a liquid-tight manner.

Embodiment 24

Consumption unit (100) according to any of embodiments 18 to 23, characterised in that
in the ready-to-use state, the support plate (23) supplements the tank housing (102) of the liquid reservoir (18) to form a complete and liquid-tight liquid tank (104).

Embodiment 25

Inhaler (27) comprising a vaporiser head (1), a consumption unit (100) and/or a liquid reservoir (18) according to any of the preceding embodiment, and a basic part (16) having an electrical energy storage device (14) for powering electrical components of the inhaler (27).

Embodiment 26

Method for producing a ready-to-use consumption unit (100) for an inhaler (27), characterised by the following steps:
providing a vaporiser head (1) according to any of embodiment 1 to 13;
providing a liquid reservoir (18) according to any of embodiment 14 to 17;
piercing the tank housing (102) of the liquid reservoir (18) using the cannula (82) of the vaporiser head (1).

Embodiment 27

Method for producing a ready-to-use consumption unit (100) according to embodiment 26, characterised by the following step:
locking the vaporiser head (1) in place on the liquid reservoir (18), in particular by means of a rotational movement.

The invention claimed is:
1. A vaporiser head for an inhaler, comprising:
a heating element-wick structure assembly,
wherein the heat element-wick structure comprises:
an electrically operable heating element, which has at least one liquid-conducting through-channel; and
a porous and/or capillary wick structure arranged at an inlet side of the electrically operable heating element;
a support plate for retaining the heating element-wick structure assembly; and
a liquid-conducting cannula having a piercing region.
2. The vaporiser head according to claim 1,
wherein the wick structure and/or the electrically operable heating element is/are arranged on an attachment side of the liquid conducting cannula.
3. The vaporiser head according to claim 1,
wherein the wick structure is arranged at least in part inside the liquid conducting cannula.
4. The vaporiser head according to claim 1,
wherein the heating element-wick structure assembly is formed as a layered assembly.
5. The vaporiser head according to claim 1,
wherein the liquid conducting cannula has a sheath extending between an attachment side of the liquid conducting cannula and a pricking side of the liquid conducting cannula, and
wherein the sheath circumferentially encases the heating element-wick structure assembly at least in part.
6. The vaporiser head according to claim 1,
wherein the piercing region is configured to pierce an external component.
7. The vaporiser head according to claim 1,
wherein the piercing region has a cutting edge.
8. The vaporiser head according to claim 1,
wherein the support plate has a through-opening.
9. The vaporiser head according to claim 8,
wherein the heating element-wick structure assembly extends at least in part through the through-opening in the support plate.
10. The vaporiser head according to claim 1, further comprising:
a locking member for locking in an external component.

11. The vaporiser head according to claim 1,
wherein the vaporiser head is configured such that a mouthpiece can be attached to the vaporiser head.
12. The vaporiser head according to claim 1,
wherein the liquid conducting cannula consists of metal.
13. The vaporiser head according to claim 1,
wherein the electrically operable heating element is a microelectromechanical system (MEMS) and/or is silicon-based.
14. A liquid reservoir, comprising:
a tank housing,
wherein the tank housing is configured to be punctured by a liquid conducting cannula.
15. The liquid reservoir according to claim 14,
wherein the tank housing comprises a piercing seal.
16. The liquid reservoir according to claim 14,
wherein the liquid reservoir is made at least in part of plastics material and/or metal capable of being punctured by the liquid conducting cannula.
17. The liquid reservoir according to claim 14, further comprising:
a locking device for locking an external component in place.
18. A consumption unit, comprising:
a vaporiser head according to claim 1; and
a liquid reservoir,
wherein the liquid reservoir comprises:
a tank housing,
wherein the tank housing is configured to be punctured by a liquid conducting cannula,
wherein the vaporiser head is configured to pierce the liquid reservoir via the liquid conducting cannula to produce a ready-to-use state of the consumption unit.
19. The consumption unit according to claim 18, further comprising:
a mouthpiece.
20. The consumption unit according to claim 19,
wherein the support plate of the vaporiser head is attached to the mouthpiece.
21. The consumption unit according to claim 19,
wherein in the ready-to-use state of the consumption unit, the liquid conducting cannula is sunk into the mouthpiece.
22. The consumption unit according to claim 18,
wherein in the ready-to-use state of the consumption unit, the support plate is aligned with the tank housing of the liquid reservoir.
23. The consumption unit according to claim 18,
wherein in the ready-to-use state of the consumption unit, the vaporiser head closes the liquid tank in a liquid-tight manner.
24. The consumption unit according to claim 18,
wherein in the ready-to-use state of the consumption unit, the support plate supplements the tank housing of the liquid reservoir to form a complete and liquid-tight liquid tank.
25. An inhaler, comprising:
a vaporiser head according to claim 1; and
a basic part having an electrical energy storage device for powering electrical components of the inhaler.
26. A method for producing a consumption unit for an inhaler in a ready-to-use state, comprising:
providing a vaporiser head according to claim 1;
providing a liquid reservoir,
wherein the liquid reservoir comprises:
a thank housing, wherein the tank housing is configured to be punctured by the liquid conducting cannula of the vaporiser head; and piercing the tank housing of the liquid reservoir using the liquid conducting cannula of the vaporiser head.

27. The method according to claim 26, further comprising:

locking the vaporiser head in place on the liquid reservoir.

\* \* \* \* \*

UNITED STATES PATENT AND TRADEMARK OFFICE
CERTIFICATE OF CORRECTION

PATENT NO. : 11,154,666 B2  
APPLICATION NO. : 16/458101  
DATED : October 26, 2021  
INVENTOR(S) : Rene Schmidt, Gunnar Niebuhr and Lasse Cornils Page 1 of 1

It is certified that error appears in the above-identified patent and that said Letters Patent is hereby corrected as shown below:

In the Claims

<u>Column 22,</u>
Line 67, Claim 26, "a thank housing," should read --a tank housing,--.

Signed and Sealed this  
Thirteenth Day of June, 2023

Katherine Kelly Vidal  
*Director of the United States Patent and Trademark Office*